US009968934B2

(12) United States Patent
Kim et al.

(10) Patent No.: US 9,968,934 B2

(45) Date of Patent: May 15, 2018

(54) TEST APPARATUS FOR FLUIDIC SAMPLE

(71) Applicant: SAMSUNG ELECTRONICS CO., LTD., Suwon-si (KR)

(72) Inventors: Dong Young Kim, Yongin-si (KR); Seung Woo Han, Busan (KR); Hyun-Suk Kang, Suwon-si (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 0 days. days.

(21) Appl. No.: 15/239,257

(22) Filed: Aug. 17, 2016

(65) Prior Publication Data

US 2017/0120236 A1 May 4, 2017

(30) Foreign Application Priority Data

Nov. 3, 2015 (KR) ........................ 10-2015-0153661

(51) Int. Cl.
*B01L 3/00* (2006.01)
*G01N 33/50* (2006.01)

(52) U.S. Cl.
CPC .............. *B01L 3/508* (2013.01); *G01N 33/50* (2013.01); *B01L 2200/025* (2013.01); *B01L 2300/06* (2013.01); *B01L 2300/1805* (2013.01)

(58) Field of Classification Search
CPC ............... B01L 3/508; B01L 2200/025; B01L 2300/06; B01L 2300/1805; B01L 2300/0816; B01L 2200/16; B01L 2300/0864; B01L 2300/087; B01L 2200/142; B01L 3/5027; B01L 3/502715; G01N 33/50; G01N 35/1095
See application file for complete search history.

(56) References Cited

U.S. PATENT DOCUMENTS

2007/0072287 A1* 3/2007 Morisette .......... B01L 3/502715 435/287.2
2010/0143963 A1* 6/2010 Pollack ............. B01L 3/502792 435/29
2015/0132860 A1* 5/2015 Cook ................. G01N 35/1079 436/501
2015/0196154 A1 7/2015 Thul et al.

* cited by examiner

*Primary Examiner* — Sally A Merkling
(74) *Attorney, Agent, or Firm* — Sughrue Mion, PLLC

(57) ABSTRACT

A fluidic sample test apparatus has a mounting part such that the temperature of a fluidic sample, which is inserted into the mounting part, is uniformly maintained. The fluidic sample test apparatus includes a main body having a mounting part into which a sample cartridge is inserted, a metal panel disposed on one surface of the mounting part, and a printed circuit board (PCB) disposed on another surface of the mounting part facing the one surface. One side of the metal panel is in contact with the PCB.

20 Claims, 8 Drawing Sheets

TEST APPARATUS FOR FLUIDIC SAMPLE

CROSS-REFERENCE TO RELATED APPLICATION(S)

This application claims priority from Korean Patent Application No. 10-2015-0153661, filed on Nov. 3, 2015 in the Korean Intellectual Property Office, the disclosure of which is incorporated herein in its entirety by reference.

BACKGROUND

1. Field

Exemplary embodiments of the present disclosure relate to a test apparatus to analyze a fluidic sample.

2. Description of the Related Art

Apparatuses and methods of analyzing fluidic samples are required in various fields including environmental monitoring, food inspection, medical diagnosis, etc. Analyses of fluidic samples may be performed by using test apparatuses for fluidic samples. Fluidic sample test apparatuses may perform an analysis of a sample by using reaction between a particular chemical substance and the sample via a biosensor, and the like.

By using a fluidic sample test apparatus, a sample cartridge including a sample to be tested may be analyzed by accommodating the sample cartridge in the fluidic sample test apparatus, and performing an analysis with a door closed. Details of the analysis, analysis stages, operating states of the analysis, or the like may be displayed on a display. Analysis results may be printed out on a printing medium. The fluidic sample test apparatus may be used for blood tests to diagnose diseases.

In general, since reaction results are significantly influenced by temperature conditions in biochemical reactions of a fluidic sample, there is a need to maintain temperature conditions required to normally perform the reactions while the reactions are performed.

SUMMARY

Apparatuses and methods consistent with exemplary embodiments provide a fluidic sample test apparatus having a mounting part such that a temperature of a fluidic sample, which is inserted into the mounting part, is uniformly maintained.

Additional aspects of the disclosure will be set forth in the description which follows. Various modifications from exemplary embodiments will be apparent to one of ordinary skill in the art without departing from the scope of the inventive concept.

In accordance with an aspect of an exemplary embodiment, a fluidic sample test apparatus includes a main body including a mounting part into which a sample cartridge is inserted, the mounting part having a first surface and a second surface facing the first surface, a metal panel disposed on the first surface of the mounting part, and a printed circuit board (PCB) disposed on the second surface of the mounting part, wherein one side of the metal panel is in contact with the PCB.

The metal panel may have at least one bent portion that contacts the PCB.

A fluidic sample test apparatus may further include a heating member mounted on a first side of the PCB.

The at least one bent portion may contact a second side of the PCB opposite to of the first side of the PCB.

The metal panel and the PCB may be spaced apart from each other to provide a space into which the sample cartridge is inserted.

The metal panel may be disposed to contact a first surface of the sample cartridge, and the PCB may be disposed to contact a second surface of the sample cartridge.

The metal panel may have a plurality of bent portions that contact the PCB.

The metal panel may be formed of a metallic material including at least one of copper and aluminum.

The mounting part may include an upper panel and a lower panel spaced apart from and facing the upper panel.

The upper panel and the lower panel may be formed of insulating materials.

The first surface of the mounting part may be a bottom surface of the upper panel, and the second surface of the mounting part may be a top surface of the lower panel.

At least one portion of the metal panel may overlap the first panel.

In accordance with an aspect of another exemplary embodiment, a fluidic sample test apparatus includes a main body including a mounting part into which a sample cartridge is inserted, the mounting part having a first surface and a second surface facing the first surface; a metal panel disposed on the first surface of the mounting part, and a substrate disposed on the second surface of the mounting part; a heating member disposed at a first side of the substrate, wherein the metal panel has at least one bent portion that contacts a second side of the substrate opposite to the first side of the substrate.

The metal panel and the substrate may be spaced apart from each other to provide a space into which the sample cartridge is inserted.

The metal panel may be disposed to contact a first surface of the sample cartridge and the substrate may be disposed to contact a second surface of the sample cartridge.

The metal panel and the substrate may be formed of a metallic material conducting heat.

In accordance with an aspect of another exemplary embodiment, a fluidic sample test apparatus includes a main body including a mounting part into which a sample cartridge is inserted, wherein the mounting part includes a first panel, a second panel spaced apart from and facing the first panel, a substrate mounted on the second panel; and a heating member disposed on the substrate, wherein the first panel has at least one metal portion made of a metallic material.

The at least one metal portion of the first panel may be in contact with one surface of the sample cartridge inserted into the mounting part.

One side of the metal portion of the first panel may be in contact with the substrate.

The first panel may have a bent portion formed by bending one portion of the metal portion and the bent portion is in contact with the substrate.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
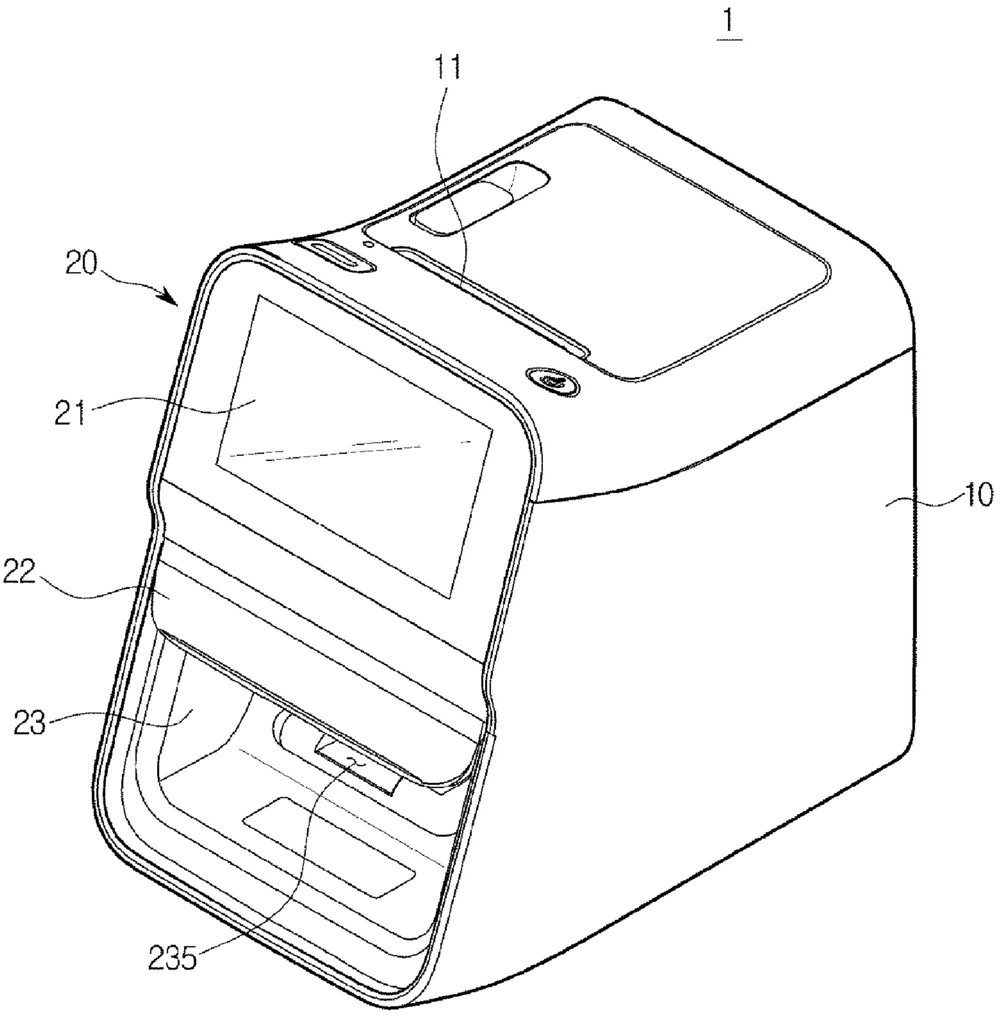
FIG. 1 is a perspective view illustrating a fluidic sample test apparatus according to an exemplary embodiment.

Reference will now be made in detail to exemplary embodiments of the present disclosure, examples of which are illustrated in the accompanying drawings, wherein like reference numerals refer to like elements throughout.

Figure 2:
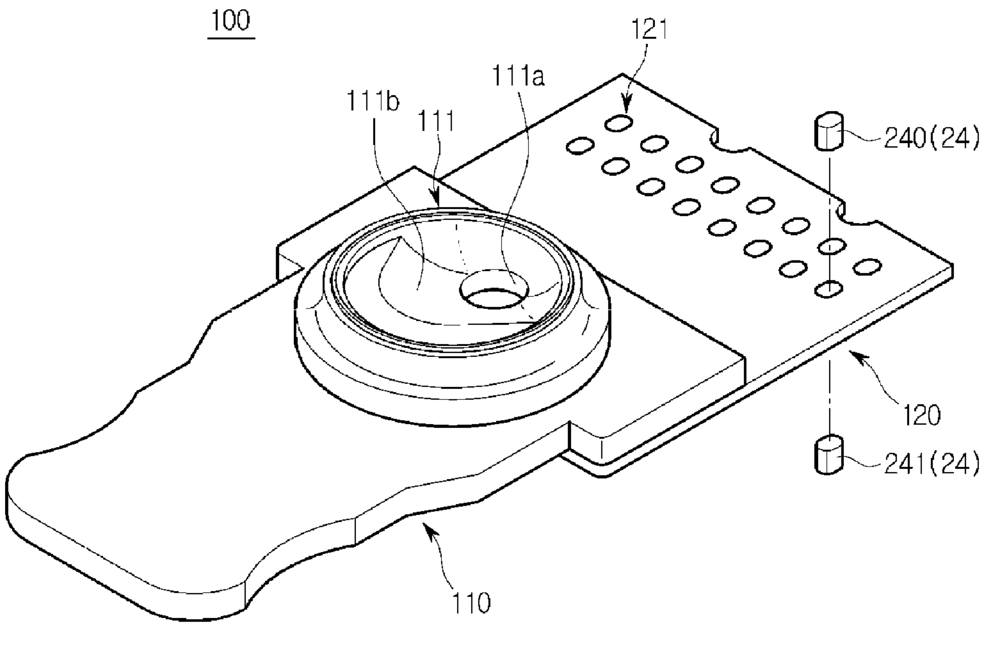
FIG. 2 is a perspective view illustrating a sample cartridge according to an exemplary embodiment.

FIG. 1 is a perspective view illustrating a fluidic sample test apparatus according to an exemplary embodiment. FIG. 2 is a perspective view illustrating a sample cartridge according to an exemplary embodiment.

Referring to FIGS. 1 and 2, the fluidic sample test apparatus 1 includes a main body 10 and a door module 20 provided in the front of the main body 10. The main body 10 may include devices required for sample analysis such as various sensors capable of analyzing a sample. The main body 10 may include an output device 11 configured to print out analysis results of the sample on a printing medium.

The door module 20 includes a display 21, a door 22, and a frame 23. The display 21 and the door 22 may be disposed in front of the frame 23. The display 21 may be disposed at an upper portion of the door 22.

The display 21 may display information about details of a sample analysis, an operating state of the sample analysis, and the like. A mounting part 235 on which a sample cartridge 100 is mounted may be disposed in the frame 23. A user may perform an analysis operation by sliding the door 22 upward to open the door 22, mounting the sample cartridge 100 on the mounting part 235, and closing the door 22.

The main body 10 may include a controller configured to control the overall operation and function of the fluidic sample test apparatus 1. The main body 10 may include a detector 24 configured to detect a sample located in the sample cartridge 100 (FIG. 2). The detector 24 may include a light emitter 240 configured to emit light to the sample cartridge 100 and a light receiver 241 configured to receive light having passed through the sample cartridge 100 or reflected by a fluidic sample located on the sample cartridge 100. Also, the main body 10 may include a temperature control device configured to control temperature such that reactions take place in the sample cartridge 100 at a predetermined temperature.

The sample cartridge 100 accommodates a fluidic sample such as blood. The user may detect the existence of a test item contained in the fluidic sample located in the sample cartridge 100 or a concentration thereof by using the fluidic sample test apparatus 1. The sample cartridge 100 may include reagents used to detect the test item in reaction with the fluidic sample.

When the sample cartridge 100 is mounted on the mounting part 235, the light emitter 240 and the light receiver 241 of the detector 24 may be arranged to face each across opposite surfaces of the sample cartridge 100. For example, the light emitter 240 may be located above the sample cartridge 100, and the light receiver 241 may be located below the sample cartridge 100. As another example, both the light emitter 240 and the light receiver 241 may also be located together above or below the sample cartridge 100.

Information detected by the detector 24 may be transmitted to the controller, and the controller may display the detection results on the display 21 or output the detection results via the output unit 11.

The sample cartridge 100 includes a housing 110 and a test portion 120 in which a reaction between a fluid and a reagent occurs.

The housing 110 may include a fluid accommodation portion 111. The fluid accommodation portion 111 may have a hole 111*a* into which a fluid is introduced and a supply assistance part 111*b*. The supply assistance part 111*b* may be inclined such that the fluid easily flows into the hole 111*a*. A filter to remove blood corpuscles from blood when blood is introduced into the hole 111*a* may be provided in the hole 111*a*.

The test portion 120 may include a plurality of chambers 121 in which liquids introduced through the fluid accommodation portion 111 are accommodated. The chambers 121 provided in the test portion 120 may include reaction chambers that accommodate reagents used to detect various types of test items and control chambers that do not include the reagents.

When serum moves to the reaction chambers containing the reagents used to detect the test items, the detector 24 may emit light to the reaction chambers, detect light having passed through the reaction chambers, and transmit detection results to the controller. The controller may acquire information about the existence of the test items or concentrations thereof by calculating absorbance based on the received detection results.

In general, in case of a biochemical reaction, temperature conditions of a space in which the reaction takes place are important for appropriate reactions. When the temperature conditions are not satisfied, reactants may be denatured or the reactions may not be properly performed, and thus a desired material may not be detected. Thus, optimal temperature conditions to normally perform the reaction while testing the fluidic sample need to be maintained in order to obtain accurate test results of the fluidic sample.

The configurations of the fluidic sample test apparatus 1 to analyze a sample and the sample cartridge 100 including chambers accommodating the sample are not limited to the embodiment illustrated in FIGS. 1 and 2, and the fluidic sample test apparatus and the sample cartridge may have various other configurations.

Figure 3:
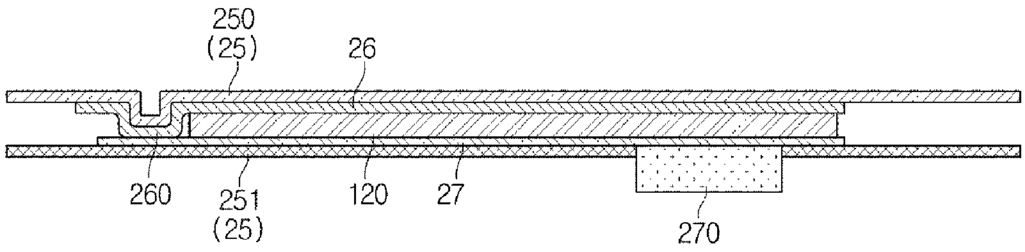
FIG. 3 is a cross-sectional view illustrating a mounting portion of the fluidic sample test apparatus, according to an exemplary embodiment, into which the sample cartridge is inserted.
Figure 4:
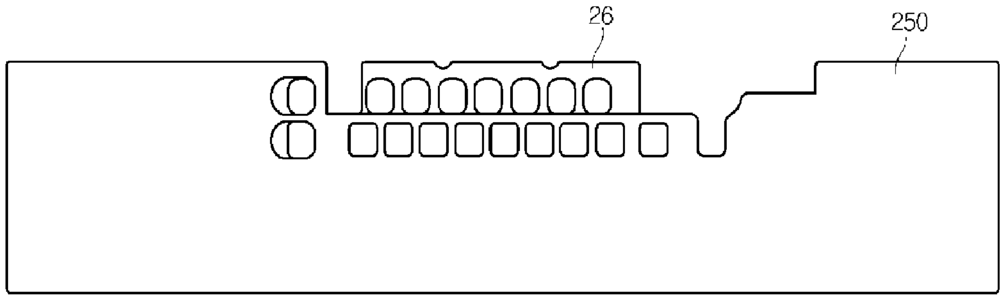
FIG. 4 is a view illustrating a part of the mounting portion of the fluidic sample test apparatus according to an exemplary embodiment.
Figure 5:
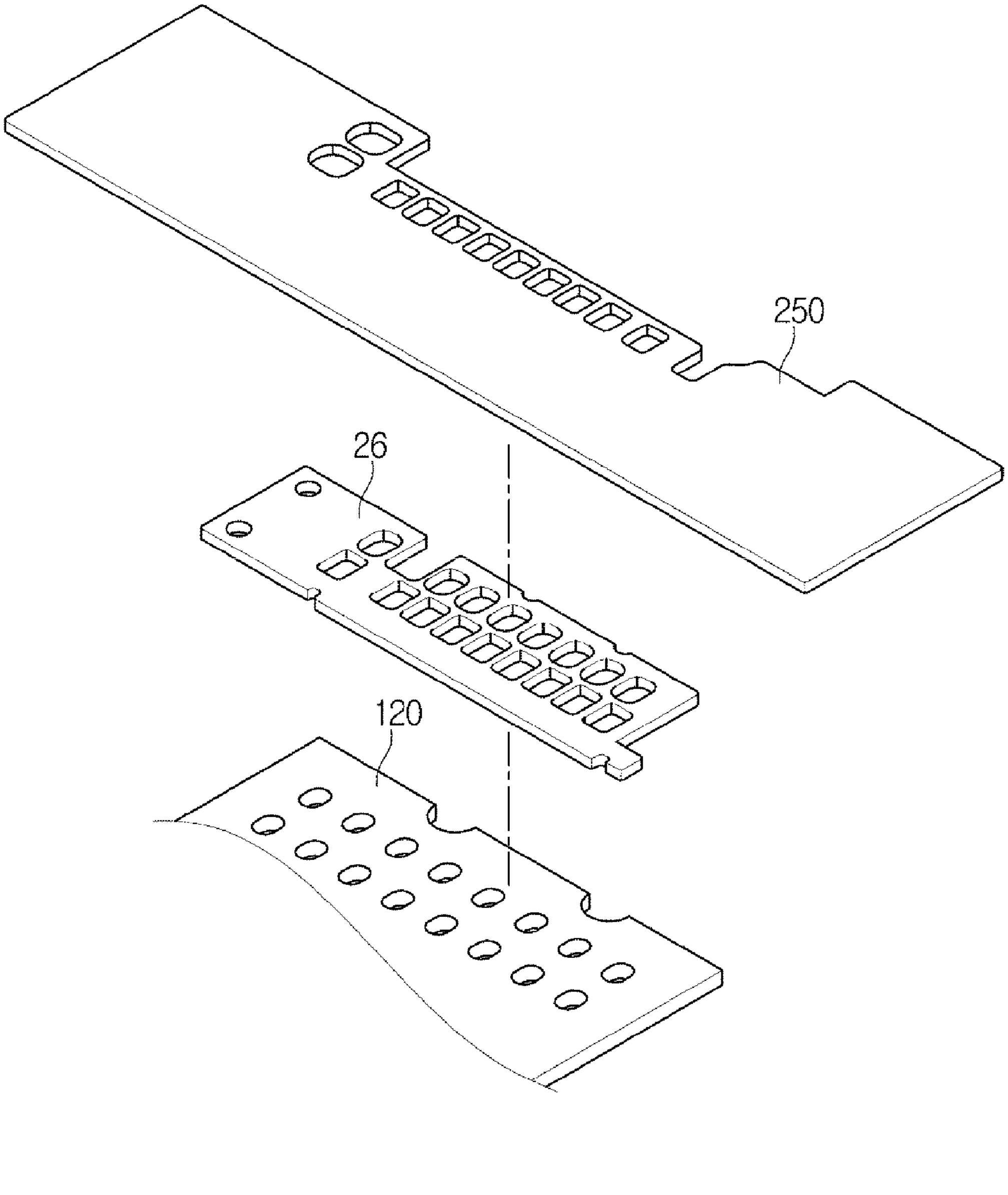
FIG. 5 is an exploded perspective view illustrating parts of the mounting portion and the sample cartridge of a fluidic sample test apparatus according to an exemplary embodiment.

FIG. 3 is a cross-sectional view illustrating a mounting portion of the fluidic sample test apparatus according to the embodiment into which a sample cartridge is inserted. FIG. 4 is a view illustrating a part of the mounting portion of the fluidic sample test apparatus according to the embodiment. FIG. 5 is an exploded perspective view illustrating parts of the mounting portion and the sample cartridge of the fluidic sample test apparatus according to an embodiment.

Referring to FIGS. 3 to 5, the fluidic sample test apparatus 1 according to exemplary embodiments includes a mounting portion 25 including the mounting part 235. The mounting portion 25 may include an upper panel 250 and a lower panel 251 facing the upper panel 250. The upper panel 250 and the lower panel 251 may be spaced apart from each other by a predetermined interval to form the mounting part 235 that includes a space into which the test portion 120 is inserted.

The upper panel 250 and the lower panel 251 may be formed of a material having a low thermal conductivity, respectively. For example, each of the upper panel 250 and the lower panel 251 may be injection-molded using an insulating material such as a plastic material.

A printed circuit board (PCB) 27 may be mounted on the lower panel 251. A heating member 270 such as a transistor (FET) may be disposed on the PCB 27. The PCB 27 may be formed of a metallic material having a high thermal conductivity. For example, the PCB 27 may be formed of a metallic material having a high thermal conductivity such as copper (Cu) or aluminum (Al).

The PCB 27 made of a metallic material having a high thermal conductivity may prevent non-uniform temperature distribution in the test portion 120 which is caused when heat is transmitted only to a portion of the test portion 120 located on the heating member 270 that is disposed at one side of the PCB 27. Heat generated by the heating member 270 may be transmitted to the entire bottom surface of the test portion 120 through the PCB 27.

Although the configuration in which heat is transmitted to the test portion 120 from the PCB 27 provided with the heating member 270 has been described above, heat may also be transmitted to the test portion 120 using a heating device such as a heater. Hereinafter, an example of transmitting heat to the test portion 120 from the PCB 27 provided with the heating member 270 will be described.

When the test portion 120 of the sample cartridge 100 is mounted on the mounting part 235, the test portion 120 may be located on the PCB 27. The test portion 120 may be mounted on the PCB 27 in direct contact with the PCB 27.

A metal panel 26 may be mounted on the bottom surface of the upper panel 250. When the test portion 120 of the sample cartridge 100 is mounted on the mounting part 235, the metal panel 26 may be located on the test portion 120. The metal panel 26 may be made of a metallic material having a high thermal conductivity such as copper (Cu) or aluminum (Al).

The metal panel 26 may be configured such that at least one portion of the metal panel 26 overlaps the upper panel 250. Although the configuration in which the metal panel 26 is provided separately from the upper panel 250 has been described above, the metal panel 26 may not be separately provided and the upper panel 250 may be formed of a metallic material.

The metal panel 26 may be separately fabricated and installed on the upper panel 250 or may be injection-molded as being inserted while the upper panel 250 is injection-molded.

The metal panel 26 may have a bent portion 260 formed by bending a portion of the metal panel 26 at one side thereof. The bent portion 260 may be in contact with the PCB 27 disposed on the lower panel 251.

A temperature of the PCB 27 provided with the heating member 270 may be higher than that of the metal panel 26. The metal panel 26 may receive heat from the PCB 27 having a higher temperature through the bent portion 260. Heat transmitted to the metal panel 26 may be transmitted to the top surface of the test portion 120 of the sample cartridge 100.

As described above, heat may be transmitted to the test portion 120 mounted on the mounting part 235 through both the top and bottom surfaces of the test portion 120. Since heat is transmitted through the top and bottom surfaces of the test portion 120, the temperature of the test portion 120 may be rapidly increased. As the temperature of the test portion 120 rapidly increases, time required to increase the temperature of a fluidic sample to an optimal temperature for analysis thereof may be reduced.

When the heating member 270 is disposed at one side of the PCB 27, one portion of the test portion 120 located on the heating member 270 may have a higher temperature than the other portions thereof. In addition, since one side of the test portion 120 may be in an environment receiving more heat from electronic parts, and the like installed in the main body 10 than the other side, the one side of the test portion 120 may have a higher temperature than the other side.

When the temperature of the test portion 120 is non-uniformly distributed as described above, reliability of the analysis results of the fluidic sample may decrease.

When the heating member 270 is disposed at one side of the PCB 27, the bent portion 260 may be disposed to be in contact with the other side of the PCB 27. For example, when the heating member 270 is disposed at the right side of the PCB 27, the bent portion 260 may be disposed at the left side of the PCB 27 in contact therewith.

Heat generated by the heating member 270 may be transmitted to the PCB 27, and the heat transmitted to the PCB 27 may be transmitted to the metal panel 26 located on the top surface of the test portion 120 via the bent portion 260.

In this regard, one side of the PCB 27 disposed under the test portion 120 where the heating member 270 is located may have a higher temperature than the other side. However, the other side of the metal panel 26 disposed on the test portion 120 where the bent portion 260 is located may have a higher temperature than the one side.

The bottom surface of the test portion 120 receives heat from the PCB 27 with one side having a higher temperature than the other side, and the top surface of the test portion 120 receives heat from the metal panel 26 with the other side having a higher temperature than the one side. Thus, heat may be uniformly transmitted to the one side and the other side of the test portion 120. Thus, temperature of the entire test portion 120 may be uniformly distributed, and reliability of the analysis results of the fluidic sample may be improved.

Similarly, when heat is non-uniformly transmitted to the test portion 120 due to inner environmental conditions of the main body 10, the position of the bent portion may be appropriately adjusted to uniformly maintain the temperature of the test portion 120.

For example, when heat is non-uniformly transmitted to the test portion 120 due to inner environmental conditions of the main body 10 after fabricating the fluidic sample test apparatus 1, heat may be uniformly transmitted to the test portion 120 efficiently by only adjusting the position of the bent portion. As the entire test portion 120 has a uniform temperature, reliability of the analysis results of the fluidic sample may be improved.

Figure 6:
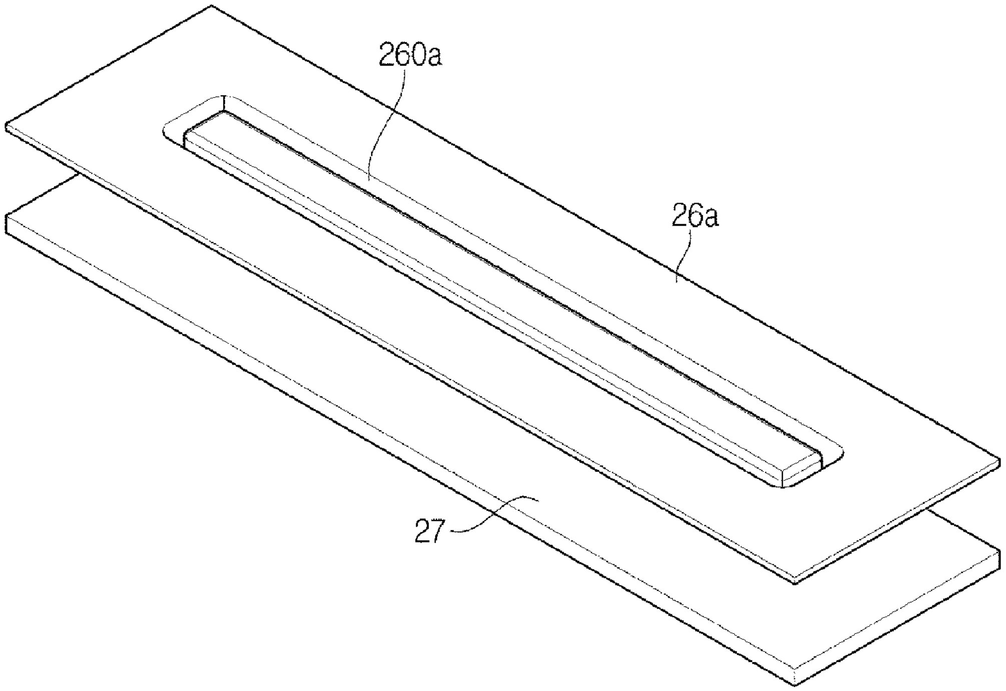
FIG. 6 is a view illustrating a mounting portion of a fluidic sample test apparatus according to another exemplary embodiment.
Figure 7:
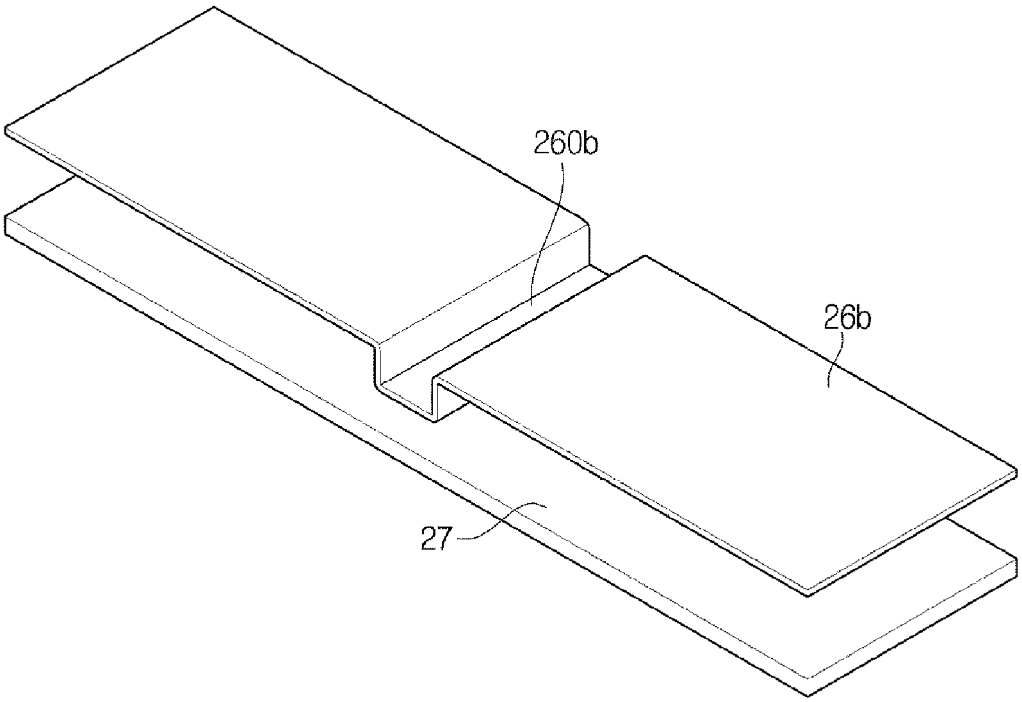
FIG. 7 is a view illustrating a mounting portion of a fluidic sample test apparatus according to another exemplary embodiment.
Figure 8:
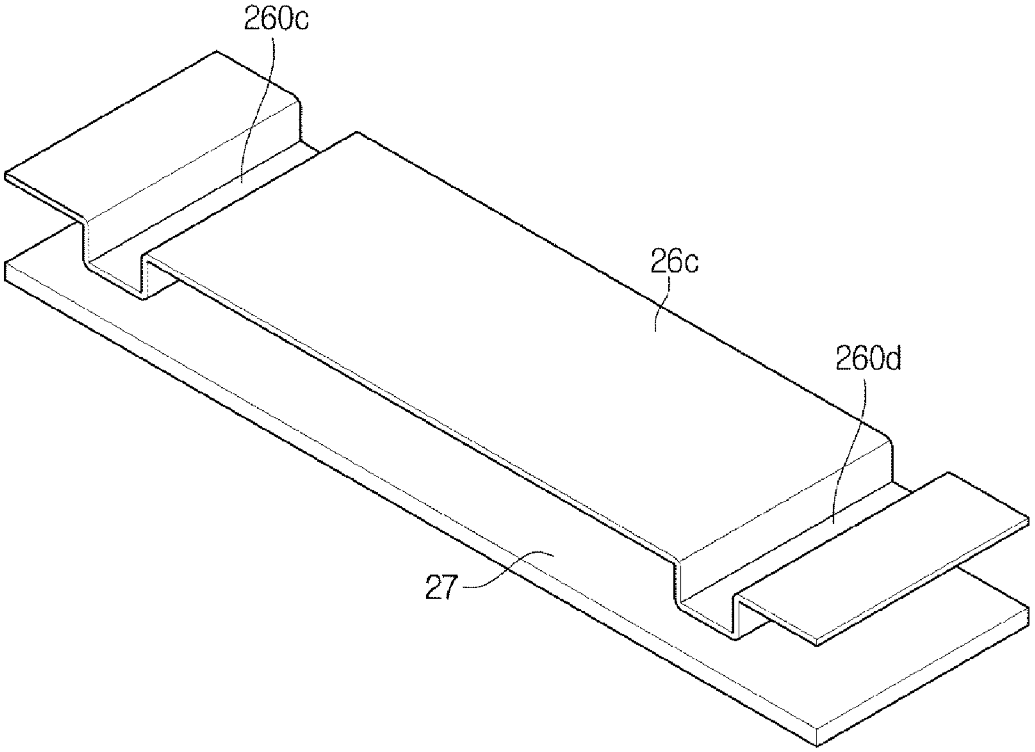
FIG. 8 is a view illustrating a mounting portion of a fluidic sample test apparatus according to another exemplary embodiment.

FIG. 6 is a view illustrating a mounting portion of a fluidic sample test apparatus according to another embodiment. FIG. 7 is a view illustrating a mounting portion of a fluidic sample test apparatus according to another embodiment. FIG. 8 is a view illustrating a mounting portion of a fluidic sample test apparatus according to another embodiment.

FIGS. 6 to 8 illustrate various shapes of the bent portion formed at the metal panel provided at the mounting portion of the fluidic sample test apparatus. The bent portion may be located at various positions of the metal panel with various shapes in accordance with environmental conditions surrounding the test portion 120 of the sample cartridge 100.

As illustrated in FIG. 6, a bent portion 260*a* may have a polygonal shape formed along an inner circumference of a metal panel 26*a*. Since the bent portion 260*a* is formed along the inner circumference of the metal panel 26*a* in the polygonal shape, heat received from the PCB 27 may be transmitted from the inner circumference of the metal panel 26*a* to the inside of the metal panel 26*a*.

Although the bent portion 260*a* illustrated in FIG. 6 has a rectangular shape formed along the inner circumference of the metal panel 26*a*, the bent portion 260*a* may also have various other shapes such as other polygonal shapes, a circular shape or an oval shape.

As illustrated in FIG. 7, a metal panel 26*b* may have a bent portion 260*b* formed at the center thereof. Since the bent portion 260*b* is formed at the center of the metal panel 26*b*, heat received from the PCB 27 may be transmitted from the center of the metal panel 26*b* to the edges of the metal panel 26*b*.

As illustrated in FIG. 8, a metal panel 26*c* may have bent portions 260*c* and 260*d* disposed at both end portions thereof. Since the bent portions 260*c* and 260*d* are disposed at both end portions of the metal panel 26*c*, heat received from the PCB 27 may be transmitted from the both end portions of the metal panel 26*c* to the center of the metal panel 26*c*.

Although the bent portions 260*b*, 260*c*, and 260*d* illustrated in FIGS. 7 and 8 have linear shapes, the shapes of the bent portions are not limited to those illustrated in FIGS. 7 and 8.

As such, the position and shape of the bent portion formed in the metal panel disposed on the upper panel 250 may vary in accordance with the environment of the mounting part 235 on which the test portion 120 of the sample cartridge 100 is mounted such that heat is uniformly transmitted to the test portion 120.

Since the metal panel is located on the top surface of the test portion 120, heat may be transmitted to the test portion 120 via the top and bottom surfaces thereof. As the bent portion is formed in contact with the PCB 27 disposed under the test portion 120 at an appropriate position of the metal panel in the form of an appropriate shape, heat received from the PCB 27 may be uniformly transmitted to the test portion 120.

Since the metal panel is disposed on the test portion and the metal panel has the bent portion in contact with the PCB 27, the temperature of the test portion 120 may be rapidly increased to a temperature suitable for analyzing the fluidic sample. In addition, since temperature is uniformly maintained in the entire test portion 120, reliability of the analysis results of the fluidic sample may be improved.

Although the configuration in which the metal panel is disposed on the upper panel side and the PCB is disposed on the lower panel side has been described above, positions of the metal panel and the PCB are not limited thereto. For example, the PCB may also be disposed on the upper panel side and the metal panel may be disposed on the lower panel side. In addition, although the configuration in which the PCB provided with the heating member is disposed on the lower panel has been described above, a metal panel provided with a heating member may also be disposed thereon.

As is apparent from the above description, the fluidic sample test apparatus according to an embodiment may uniformly maintain the temperature of the entire fluidic sample.

In addition, the fluidic sample located in the test apparatus may rapidly reach an appropriate temperature.

Although a few embodiments of the present disclosure have been shown and described, it would be appreciated by those skilled in the art that changes may be made in exemplary embodiments without departing from the principles and spirit of the inventive concept, the scope of which is defined in the following claims and their equivalents.

What is claimed is:

1. A fluidic sample test apparatus comprising:

a main body comprising a mounting part into which a sample cartridge is inserted, the mounting part having a first surface and a second surface facing the first surface;

a metal panel disposed on the first surface of the mounting part; and a printed circuit board (PCB) disposed on the second surface of the mounting part, wherein one side of the metal panel is in contact with the PCB.

2. The fluidic sample test apparatus according to claim 1, wherein the metal panel has at least one bent portion that contacts the PCB.

3. The fluidic sample test apparatus according to claim 2, further comprising a heating member mounted on a first side of the PCB.

4. The fluidic sample test apparatus according to claim 3, wherein the at least one bent portion contacts a second side of the PCB that is opposite to the first side of the PCB.

5. The fluidic sample test apparatus according to claim 2, wherein the metal panel and the PCB are spaced apart from each other to provide a space into which the sample cartridge is inserted.

6. The fluidic sample test apparatus according to claim 2, wherein the metal panel is disposed to contact a first surface of the sample cartridge, and the PCB is disposed to contact a second surface of the sample cartridge.

7. The fluidic sample test apparatus according to claim 2, wherein the metal panel has a plurality of bent portions that contact the PCB.

8. The fluidic sample test apparatus according to claim 1, wherein the metal panel is made of a metallic material comprising at least one of copper and aluminum.

9. The fluidic sample test apparatus according to claim 1, wherein the mounting part comprises an upper panel and a lower panel spaced apart from and facing the upper panel.

10. The fluidic sample test apparatus according to claim 9, wherein the upper panel and the lower panel are made of insulating materials.

11. The fluidic sample test apparatus according to claim 9, wherein the first surface of the mounting part is a bottom surface of the upper panel, and the second surface of the mounting part is a top surface of the lower panel.

12. The fluidic sample test apparatus according to claim 9, wherein at least one portion of the metal panel overlaps the upper panel.

13. A fluidic sample test apparatus comprising:

a main body having a mounting part into which a sample cartridge is inserted, the mounting part having a first surface and a second surface facing the first surface;

a metal panel disposed on the first surface of the mounting part; and a printed circuit board (PCB) disposed on the second surface of the mounting part;

a heating member disposed at a first side of the PCB, wherein the metal panel has at least one bent portion that contacts a second side of the PCB that is opposite to the first side of the PCB.

14. The fluidic sample test apparatus according to claim 13, wherein the metal panel and the PCB are spaced apart from each other to provide a space into which the sample cartridge is inserted.

15. The fluidic sample test apparatus according to claim 14, wherein the metal panel is disposed to contact a first surface of the sample cartridge and the PCB is disposed to contact a second surface of the sample cartridge.

16. The fluidic sample test apparatus according to claim 13, wherein the metal panel and the PCB are made of a metallic material conducting heat.

17. A fluidic sample test apparatus comprising:

a main body having a mounting part into which a sample cartridge is inserted;

wherein the mounting part comprises:

a first panel;

a second panel spaced apart from and facing the first panel;

a printed circuit board (PCB) mounted on the second panel; and a heating member disposed on the PCB, wherein the first panel has at least one metal portion made of a metallic material.

18. The fluidic sample test apparatus according to claim 17, wherein the at least one metal portion of the first panel is in contact with one surface of the sample cartridge inserted into the mounting part.

19. The fluidic sample test apparatus according to claim 17, wherein one side of the metal portion of the first panel is in contact with the PCB.

20. The fluidic sample test apparatus according to claim 17, wherein the first panel has a bent portion formed by bending one portion of the metal portion and the bent portion is in contact with the PCB.

* * * * *